United States Patent
Young et al.

(10) Patent No.: US 6,322,518 B1
(45) Date of Patent: *Nov. 27, 2001

(54) METHOD AND APPARATUS FOR MEASURING CARDIAC OUTPUT

(75) Inventors: Robert L. Young, Waukesha; Donald J. Melnikoff, Franklin, both of WI (US)

(73) Assignee: Heska Corporation, Ft. Collins, CO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/020,475

(22) Filed: Feb. 9, 1998

Related U.S. Application Data (63) Continuation-in-part of application No. 08/546,246, filed on Oct. 20, 1995, now Pat. No. 5,715,816, which is a continuation-in-part of application No. 08/412,287, filed on Mar. 28, 1995, now Pat. No. 5,743,261, which is a continuation-in-part of application No. 08/163,052, filed on Dec. 6, 1993, now Pat. No. 5,417,207.

(60) Provisional application No. 60/045,006, filed on Apr. 25, 1997, and provisional application No. 60/067,810, filed on Dec. 5, 1997.

(51) Int. Cl.[7] .................................................. A61B 05/00
(52) U.S. Cl. ............................ 600/505; 600/547; 600/593
(58) Field of Search ................................. 600/505, 547, 600/593

(56) References Cited

U.S. PATENT DOCUMENTS

| | | |
|---|---|---|
| Re. 31,377 | 9/1983 | Mylrea et al. . |
| 3,340,867 | 9/1967 | Kubicek et al. . |
| 3,734,094 | 5/1973 | Calinog . |
| 3,951,136 | 4/1976 | Wall . |
| 4,090,518 | 5/1978 | Elam . |
| 4,176,660 | 12/1979 | Mylrea et al. . |
| 4,214,593 * | 7/1980 | Imbruce et al. ..................... 600/593 |
| 4,349,031 | 9/1982 | Perlin . |
| 4,369,794 | 1/1983 | Furler . |
| 4,450,527 | 5/1984 | Sramek . |
| 4,476,872 | 10/1984 | Perlin . |
| 4,640,298 | 2/1987 | Pless et al. . |
| 4,817,611 | 4/1989 | Arzbaecher et al. . |
| 4,836,214 * | 6/1989 | Sramek ................................ 600/526 |
| 4,848,352 | 7/1989 | Pohndorf et al. . |
| 4,852,580 * | 8/1989 | Wood .................................. 600/547 |
| 4,930,521 | 6/1990 | Metzger et al. . |
| 4,967,759 | 11/1990 | Teves . |
| 5,000,190 * | 3/1991 | Petre .................................. 600/526 |
| 5,048,532 * | 9/1991 | Hickey et al. ...................... 600/593 |
| 5,056,532 * | 10/1991 | Hull et al. .......................... 600/380 |
| 5,092,339 * | 3/1992 | Geddes et al. ..................... 600/547 |

(List continued on next page.)

FOREIGN PATENT DOCUMENTS

| | | |
|---|---|---|
| 0366127 | 5/1990 | (EP) . |
| 1454066 | 10/1976 | (GB) . |
| 9629927 | of 0000 | (WO) . |

Primary Examiner—Robert L. Nasser
(74) Attorney, Agent, or Firm—Snell & Wilmer (57) ABSTRACT

An esophageal probe useful for invasively monitoring the cardiac output of a patient generally comprises a chassis with an electrical cable extending from the proximal end of the chassis and with the cable terminating at an electrical plug configured for connection to a cardiac output monitor. The probe includes an electrode assembly configured to generate and transmit electrical signals that are indicative of the impedance variation of the thorax. The probe further includes a deployment device attached to the chassis for stabilizing the probe within the esophagus. The probe may also be configured to include other sensing devices, for example, a temperature measuring device and an acoustic monitor.

17 Claims, 4 Drawing Sheets

U.S. PATENT DOCUMENTS

| | | |
|---|---|---|
| 5,109,851 | 5/1992 | Jadvar et al. . |
| 5,154,387 | 10/1992 | Trailer . |
| 5,170,803 | 12/1992 | Hewson et al. . |
| 5,179,952 | 1/1993 | Buinevicius et al. . |
| 5,275,162 | 1/1994 | Edwards et al. . |
| 5,309,917 | 5/1994 | Wang et al. . |
| 5,329,922 | 7/1994 | Atlee, III . |
| 5,357,954 | 10/1994 | Shigezawa et al. . |
| 5,394,880 * | 3/1995 | Atlee et al. .......................... 607/124 |
| 5,423,326 | 6/1995 | Wang et al. . |
| 5,443,073 | 8/1995 | Wang et al. . |
| 5,715,816 * | 2/1998 | Mainiero et al. .................... 600/322 |

* cited by examiner

METHOD AND APPARATUS FOR MEASURING CARDIAC OUTPUT

CROSS-REFERENCES TO RELATED APPLICATIONS

This is a continuation-in-part of U.S. Ser. No. 08/546,246 filed Oct. 20, 1995, now U.S. Pat. No. 5,715,816 issued Feb. 10, 1998, which in turn was a continuation-in-part of U.S. Ser. No. 08/412,287 filed Mar. 28, 1995, now U.S. Pat. No. 5,743,261 issued Apr. 28, 1998, which in turn was a continuation-in-part of U.S. Ser. No. 08/163,052 filed Dec. 6, 1993, now U.S. Pat. No. 5,417,207 issued May 23, 1995; furthermore, this is an application claiming priority on a prior pending Provisional Application, U.S. Serial No. 60/045,006 filed Apr. 25, 1997 and provisional application U.S. Serial No. 60/067,810, filed Dec. 5, 1997.

TECHNICAL FIELD

The present invention relates, generally, to the evaluation of cardiac functions, and more particularly to the invasive determination of cardiac output utilizing impedance cardiography.

BACKGROUND OF THE INVENTION

Impedance cardiography has been and continues to become an increasingly important mechanism for determining patient condition both during and following medical procedures.

Impedance cardiography can be considered to fall within the more general category of impedance plethysmography, which refers to the measurement of volume (and thereby flow) changes in the body, as derived from observing changes in electrical impedance. Impedance cardiography is generally known as a noninvasive bioimpedance method for measuring cardiac output. Existing cardiac output measurements are based on the principal that blood is a conductor of electricity and that the electrical impedance of the thorax will change during a cardiac cycle. This change in impedance is caused by the thoracic aortic blood flow which is directly related to the amount of blood ejected from the heart.

U.S. Pat. No. 3,340,867, now Re. 30,101, reissued September 1979 to Kubicek, et al., discloses a method for determining cardiac output by measuring the patient's heart stroke volume. There, an impedance plethysmograph employs two sets of electrodes placed on the neck and chests of patients, to provide an impedance difference signal from the two center electrodes. A constant, low-amplitude, high-frequency alternating current is applied to the outermost pair of electrodes while the innermost pair of electrodes senses the voltage levels above and below the patient's heart. Kubicek's method entails first determining the heart stroke volume from these impedance signals, based on the observation that resistance to a current passed through the chest varies with thoracic aortic blood flow, and from this determination of stroke volume, then estimating the cardiac output.

U.S. Pat. No. 4,450,527, issued to Sramek on May 22, 1984, generally discloses a similar apparatus, model and equation for relating impedance and stroke volume to determine cardiac output. U.S. Pat. No. 5,309,917, issued May 10, 1994, U.S. Pat. No. 5,423,326 issued Jun. 13, 1995, and U.S. Pat. No. 5,443,073 issued Aug. 22, 1995, all of which were issued to Wang, et al., each generally disclose variations of the Kubricek and Sramek methods.

Yet another model and method of impedance cardiography regarding the placement and spacing of electrodes has been proposed by Bernstein. According to Bernstein, stroke volume (SV) is related to the change in impedance (Z) as shown in Equation 1:

$$SV = \frac{\delta \times (0.17H)^3 \times T_{LVE} \times (dZ/dt)_{max}}{4.2 \times Z_0} \quad (1)$$

SV = Stroke Volume
$\delta$ = correction factor for patient weight
H = Patient height (cm)
$T_{LVE}$ = left ventricular ejection time (sec)
$(dZ/dt)_{max}$ = maximum value of the first derivative of Z, where Z is the change in impedance caused by thoracic aortic blood flow
$Z_0$ = mean baseline impedance of the thorax (ohm)

While each these methods can be helpful in determining cardiac output, the various types of non-invasive devices disclosed such as the outer skin electrodes of Kubicek and Sramek, often prove inefficient, for example when dealing with many surgical procedures or with skin abrasion patients. As one can imagine, these devices require a number of exposed connective wires and corresponding electrodes that may interfere with other surgical procedures. Furthermore, because the inner surface electrodes may receive impedance signals from various other regions within the patient due to the distance in placement of the electrodes from the thoracic aorta region, accuracy concerns have been raised. Additionally, incorrect electrode placement can result due to the changes in the patient's physiology of the thorax with respect to the placement of the electrodes on the sternum, as well as due to the size of the patient. Finally, as recognized in Equation 1, a correct factor for patient weight, $\delta$, must be utilized in calculating cardiac output, and often if the weight cannot be accurately determined, the weight estimation can be another source of inaccuracy.

Several of the problems with prior art non-invasive devices have been addressed by more recent developments; however, these new developments still fall short in many critical areas. For example, U.S. Pat. No. 4,836,214, issued to Sramek on Jun. 6, 1989, generally relates to an esophageal probe comprised of an array of electrical bioimpedance ring electrodes provided on a hollow, flexible tube that is insertable into the esophagus of a patient and positioned proximate the descending thoracic aorta. The Sramek device, however, like the other non-invasive prior art probes, still permits movement of the probe within the esophagus. As a result of this motion artifact, inaccuracies are possible. This problem may be further attenuated by the use of the disclosed ring electrodes in that such electrodes often tend to float within the esophagus.

U.S. Pat. No. 5,357,954, issued to Shigezawa et al. on Oct. 25, 1994, generally relates to an esophageal blood oxygen saturation probe with temperature and sound sensing devices for invasively monitoring a patient. The patent purports to suggest discloses that the internal walls of the esophagus will tend to collapse onto the outer surface of the probe's chassis and sound sensor, such that the probe's sensors will not move appreciably with respect to the esophagus. The ability of the esophagus to prevent undesirable movement of the probe as so disclosed, particularly given the size of the probe, is questioned. Nevertheless, because the probe is not substantially fixed relative a to the esophagus, there still exits an opportunity for undesirable movement which, as will be appreciated by those skilled in the art, can lead to inefficient and less accurate results.

Motion limiting devices such as those disclosed in prior oximetry work of the present assignee are known; however, heretofore teachings have not been used in impedance cardiography applications. In this regard, the subject matter of application Ser. No. 60/045,006, application Ser. No. (U.S. Pat. No. 5,715,816), application Ser. No. 08/412,287 (U.S. Pat. No. 5,743,261) and U.S. Pat. No. 5,417,207 are incorporated herein by reference.

There exists a long felt need, as one skilled in the art will appreciate, for an esophageal probe utilized in impedance cardiography that greatly reduces the movement of the catheter within the esophagus, with little or no motion artifacts. Furthermore, there exists a long felt need for improved electrodes that positively address the limitations of presently known electrodes.

SUMMARY OF THE INVENTION

An invasive esophageal probe according to the present invention addresses many of the shortcomings of the prior art.

In accordance with one aspect of the present invention, an electrode assembly is suitably disposed on an elongated, flexible chassis. The chassis is suitably configured for insertion into the esophagus of a patient. Furthermore, the electrode assembly includes prominent-arena electrodes for the delivery of alternating current and the sensing of voltage abstract associated with a corresponding impedance variation of the thorax of a patient.

In accordance with a further aspect of the present invention, the probe is suitably configured for insertion in the esophagus, and as such, includes a deployment device suitably configured as a crico-pharyngeal ("CP") "lock" which substantially secures the probe and the prominent-arena electrodes within the esophagus, greatly minimizing probe movement and enhancing the accuracy of measurement of bioimpendence signals. The CP lock also serves as an esophageal diopter which serves to prevent fluids and other matter from passing-up and being aspirated by the patient.

In accordance with a further aspect of the present invention, the probe is suitably configured to include a temperature measuring device and an acoustic diaphragm for additional monitoring capabilities.

BRIEF DESCRIPTION OF THE DRAWING FIGURES

The present invention will be hereinafter described in conjunction with the appended drawing figures, wherein like designations denote like elements, and.

DETAILED DESCRIPTION OF PREFERRED EXEMPLARY EMBODIMENTS

Figure 1:
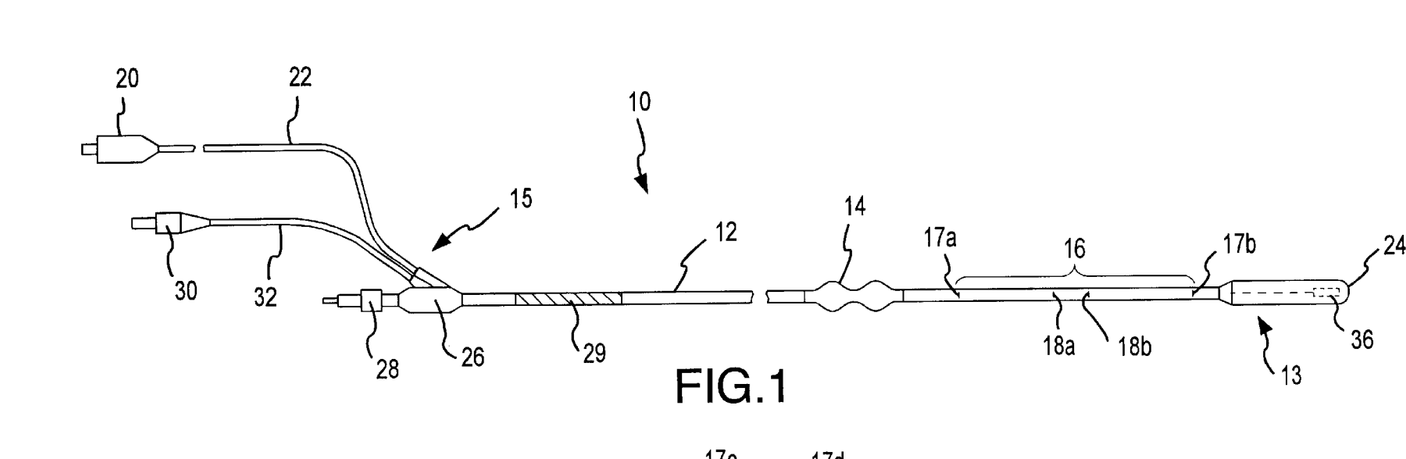
FIG. 1 is a top view of a probe in accordance with the present invention.

Referring now to FIG. 1, in accordance with a preferred embodiment of the present invention, an exemplary probe assembly 10 suitably comprises a chassis 12 having a distal end 13 and a proximal end 15, a deployment device 14, and an electrode assembly 16. Preferably, electrode assembly 16 is comprised of prominent-arena electrodes that include of at least a pair of delivery electrodes 17a and 17b and at least a pair of sensing electrodes 18a and 18b. Electrode assembly 16 is suitably interfaced with an electrode plug assembly 20 which is suitably configured for interaction with a cardiac output monitor (not shown) serving to deliver a constant, low amplitude, high frequency alternating current to respective delivery electrodes 17a and 17b and receive corresponding voltage signals from respective sensing electrodes 18a and 18b. Electrode plug assembly 20 may be advantageously attached to chassis 12 via a cable guide 26 which securely grabs an electrode cable 22 and thus provides a sealed strain relief for connection of electrode cable 22 to corresponding prominent-arena electrodes 17, 18.

In accordance with a preferred exemplary embodiment of the present invention, probe assembly 10 may also include other features. For example, probe 10 probe 10 preferably may include, in addition to the aforementioned elements, a temperature measuring device 36 and a functional diaphragm 24, and/or various combinations thereof. As shown best in FIG. 1, temperature measuring device 36 may be suitably attached to probe 10 proximate distal end 13. Preferably, device 36 comprises a thermistor, preferably of conventional configuration and design, and, as will be appreciated by those skilled in the art, is useful in determining internal body temperature of the patient. With momentary reference to FIG. 3, preferably thermistor 36 is suitably attached to a connector 30 for interface with a monitor (not shown) via respective cable sections 32 and 34. As shown best in FIG. 1, preferably section 34 is placed inside of chassis 12, while section 32 preferably, extends exteriorly of chassis 12; preferably, sections 32 and 34 are integrally connected.

With continued reference to FIG. 1, functional diaphragm 24 also may be located at distal end 13 to provide guidance of the probe 10 during insertion into the esophagus. Functional diaphragm 24 may also be suitably configured to additionally serve as an acoustic monitor, and thus, is preferably comprised of a thin acoustic material which allows for the efficient transmission of acoustic signals through chassis 12 and into an acoustic adapter 28 located about proximal end 15 of probe 10. As shown best in FIG. 1, acoustic adapter 28 is suitably mounted on proximal end 15 of probe 10 to interface with a standard medical microphone. (not shown) In addition, diaphragm 24 may be suitably configured to house thermistor 36 and to seal distal end 13 of probe 10.

Electrodes 17a and 17b and electrodes 18a and 18b are suitably embedded in chassis 12 such that probe 10 can deliver alternating current and then detect a voltage abstract associated with an impedance variation of the thorax, with the results measured at a cardiac output monitor (not shown). Preferably, delivery electrode 17a is positioned in close proximity and distal to deployment device 14 while delivery electrode 17b is positioned in proximity to distal end 13 of probe 10. Furthermore, sensing electrodes 18a and 18b are positioned in between delivery electrodes 17a and 17b, and are spaced approximately equivalent to a patient's heart, to suitably receive the appropriate voltage abstract associated with the impedance variation of the thorax.

Figures 2, 3:
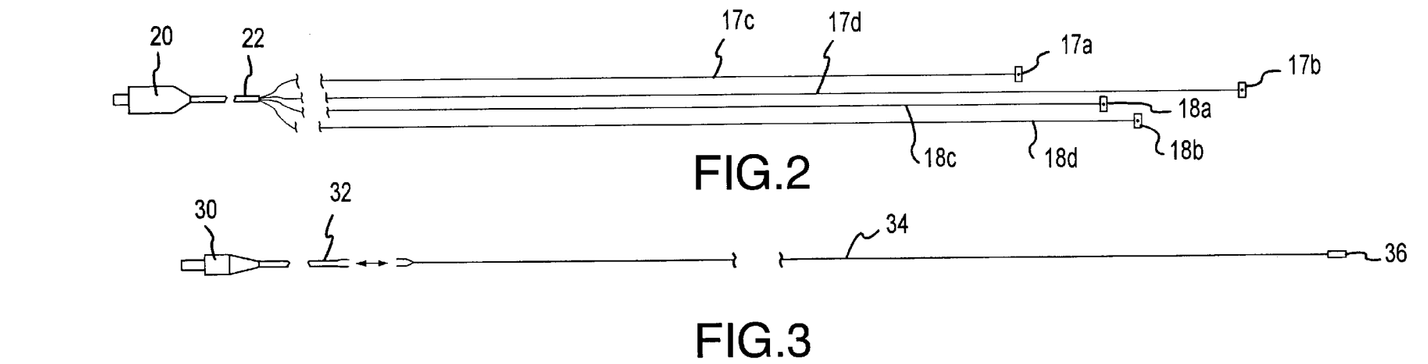
FIG. 2 shows a schematic representation of an electrode assembly in accordance with the present invention.
FIG. 3 shows a schematic representation of a temperature measuring device in accordance with the present invention.

Referring now to FIG. 2, delivery electrode 17a and 17b and sensing electrodes 18a and 18b are suitably connected to electrode wires, 17c and 17d and 18c and 18d, respectively. Preferably, this connection to the electrode wires is by soldering. Furthermore, each electrode wire is fed through chassis 12 and deployment device 14 and into cable guide 26 for further attachment to electrode cable 22. In accordance with a particularly preferred aspect of this preferred embodiment, each electrode wire may be spiral wound into chassis 12. Furthermore, electrode wires are located within cable 22 which suitably provides a biocompatible sheath for further protection.

Figure 6A:
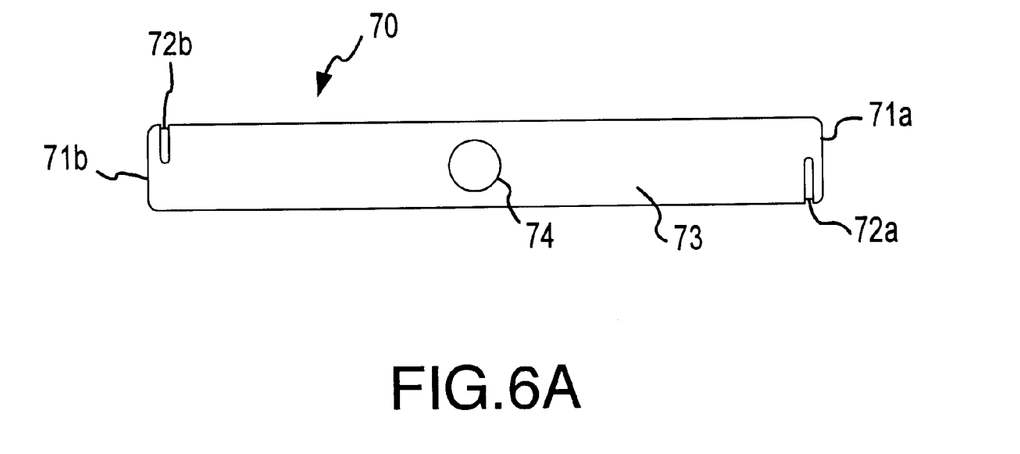
FIG. 6A shows an exploded view of a typical electrode suitable for use in accordance with the probe in accordance with the present invention; and, FIG. 6B is a side view of the electrode of FIG. 6A.
Figure 6B:
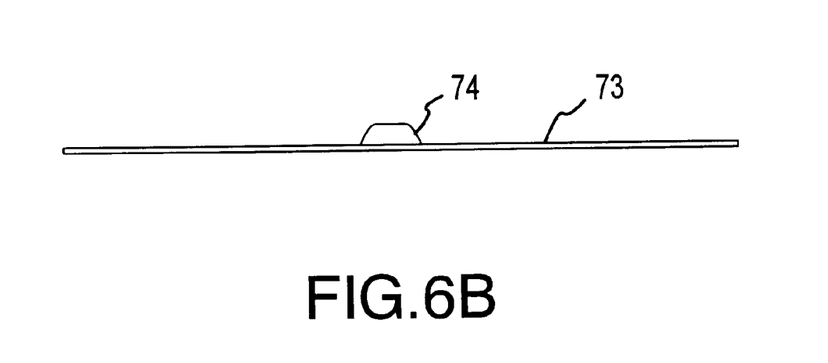

Referring momentarily to FIG. 6, and in accordance with a further aspect of the present invention, each electrode of electrode assembly 16 suitably comprises a conductive band 70, which possesses a first end 71a, a second end 71b, an outside surface 73, and a contact surface 74. Furthermore, in accordance with a preferred aspect of the present invention, first end 71a and second end 71b each are suitably provided with respective slots 72a and 72b, designed to enable attachment of conductive band 70 to chassis 12. Additionally, contact surface 74 is suitably configured to enable the electrode assembly 16 to achieve and maintain contact with the esophagus region. In accordance with this preferred aspect, contact surface 74 may be produced by a mechanical punch formed from outside surface 73. Alternatively, contact surface 74 may be suitably formed and then attached to the conductive band 70 by any other means, such as, for example, by direct soldering to the outside surface 73 of conductive band 70. It should be appreciated that bands 70 may be formed in other configurations or attached to chassis 12 in other manners, as is now known or hereafter devised by those skilled in the art.

In accordance with a preferred embodiment of the present invention, chassis 12 is suitably configured to be removably inserted into an anatomical canal (e.g. the esophagus) of a human or animal. Chassis 12 is suitably made from any desired biocompatible material, for example, polyurethane, polyethylene, PVC, PTFE, and/or the like. In accordance with a particularly preferred embodiment, chassis 12 is suitably comprised of a flexible resiliency to minimize the danger of lacerating the esophagus during insertion.

In accordance with a preferred aspect of this further embodiment of the present invention, chassis 12 is of sufficient length to position the various components thereon at optimal positions within the esophageal or other anatomical cavity. In accordance with various aspects of the present invention, chassis 12 evidences a length in the range of about 25 to about 75 cm, and preferably in the range of about 45 to about 65 cm, and most preferably in the range of about 52 to about 54 cm.

In accordance with the present invention, and as fully disclosed in commonly assigned pending application U.S. Ser. No. 08/546,246, entitled, "Improved Oximeter Probes and Methods for the Invasive Use Thereof", probe assembly 10 may be suitably configured to ensure that the probe 10 is effectively stabilized within a body cavity. For example, by enlarging the diameter of the chassis 12 or otherwise deploying prominentarena electrodes 17, 18 of probe into engagement with a wall of the anatomical canal into which the probe is inserted, a certain degree of stabilization may be obtained.

In accordance with this aspect of the present invention, probe 10 is preferably configured such that the prominent-arena electrodes are positioned and maintained in a region proximate the thoracic aorta. For example, the present inventors have found that locking the probe in a muscular region of a body canal enables the measurement of bioimpedence signals which is relatively unaffected by movements. In accordance with a preferred aspect, the muscle targeted comprises a sphincter-type muscle, such as, the crico-pharyngeal (CP) muscle in the esophagus. As will be appreciated, such sphincter-type muscles function, such as when food or other objects approach the muscle, to contract and dilate thereby allowing the objects to pass. After the objects pass, the muscle again relaxes and constricts.

Thus, in accordance with the various aspects of this embodiment of the invention, probe 10 is suitably configured to take advantage of the dilation and constriction of such muscle, e.g. the CP or other similar muscle, to secure and stabilize the probe within the anatomical canal, thus tending to inhibit movement of the probe while obtaining reliable bioimpedence readings. Such a configuration also serves to act as an esophageal diopter, preventing fluids and other matter from passing up and being aspirated by a patient. With momentary reference to FIG. 5, when in place, the preferred configurations of probe 10 enable stabilization of probe 10 in the crico-pharyngeal ("CP") muscle region 92 which is between the hypo-pharynx 94 and esophageal opening 90, approximately 13 cm to 15 cm from the back incisors of a typical adult.

In accordance with this aspect of the preferred embodiment of the present invention, deployment device 14 preferably comprises an integrally formed stabilizing member, and as a result of the configuration of device 14, probe 10 is suitably and stably deployed within the desired body cavity. In such case, deployment device 14 may be made of any bio-compatible material suitable for use within a body cavity. In accordance with a preferred embodiment of the present invention, deployment device 14 may be constructed of soft polyvinyl chloride (PVC) having a durometer in the range of about 15 to about 60, more preferably in the range of about 25 to about 35, and optimally about 30.

Figure 4A:
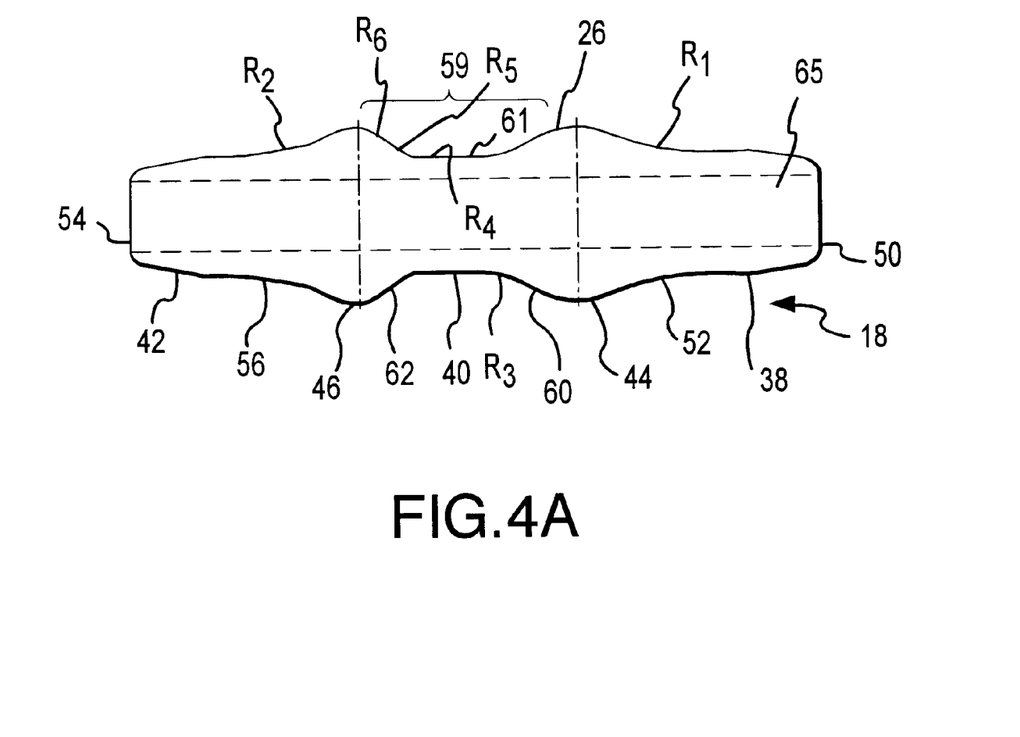
FIG. 4A is a side view showing a preferred configuration of a deployment device useful in connection with a probe in accordance with the present invention.
Figure 4B:
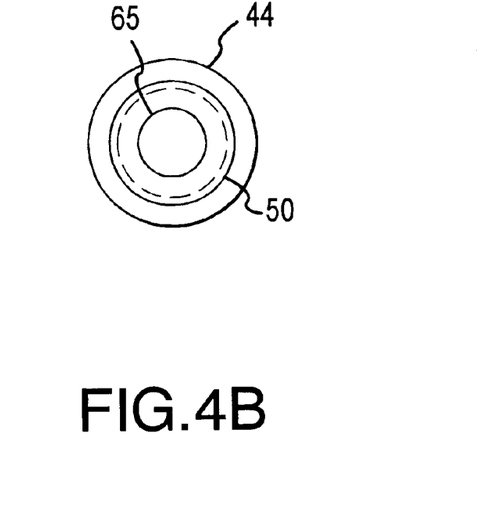
FIG. 4B is an end view of the deployment device of FIG. 4A.

Referring now to FIGS. 4A and 4B, and in accordance with a preferred aspect of this embodiment of the present invention, deployment device 14 may be a conformalshaped tube having two enlarged lobes 44 and 46. Preferably, device 14 includes in seriatim, a first segment 38, first lobe 44, a second segment 40, second lobe 46 and a third segment 42. First segment 38 suitably includes a leading edge 50 and a substantially smooth sloped outer surface 52 evidencing a radius $R_1$ which terminates in lobe 44. Similarly, third segment 42 suitably includes a trailing edge 54 and a substantially smooth outer sloped surface 56 evidencing a radius $R_2$ which terminates in lobe 46. Second segment 40 suitably interconnects lobes 44 and 46 and preferably extends from the crest of lobe 44 to the crest of lobe 46. Segment 40 preferably evidences a substantially smooth sloped outer surface 59 which is preferably defined by a plurality of radii. In accordance with a particularly preferred aspect of this embodiment of the present invention, surface 59 is defined by respective radii $R_3$, $R_4$, $R_5$ and $R_6$ which cooperate to form an inner constricted region 61 bounded by respective outwardly extending sloped regions 60 and 62. As shown in FIG. 4A, device 14 so configured preferably evidences a generally circumferentially symmetrical hourglass configuration. However, preferably, leading lobe 44 and trailing lobe 46 have different configurations to advantageously secure device 14 within the desired anatomical canal.

Figure 5:
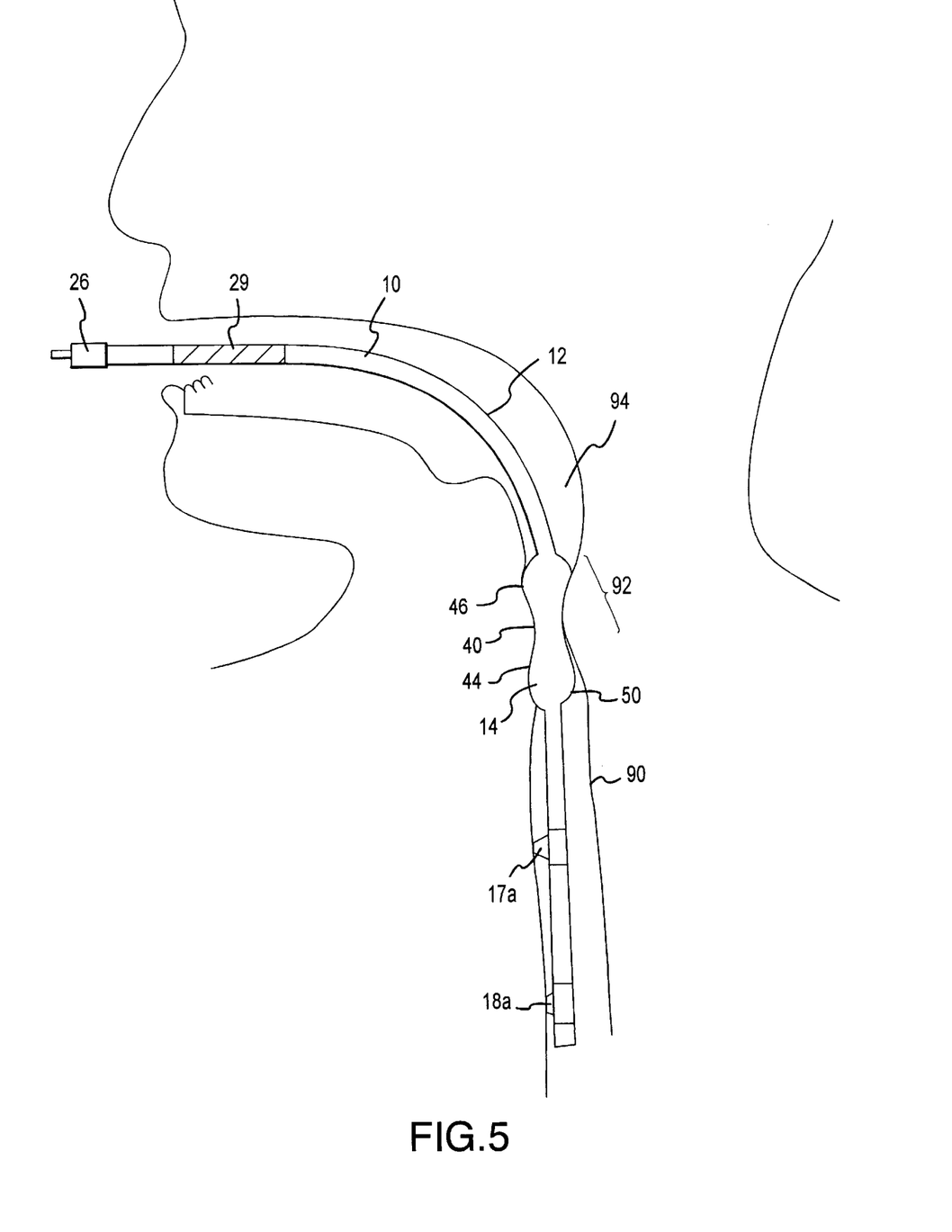
FIG. 5 shows a schematic representation of the probe of FIG. 1 within an anatomical canal (e.g. the esophagus) of a patient.

To aid in the description of this aspect of the present invention, and with continued reference to FIG. 4A and momentary reference to FIG. 5, the use of device 14 will now be briefly described. When deployment device 14 is inserted into an anatomical canal, e.g. the esophagus, leading edge 50 enters into a muscle region, e.g. the CP muscle region, thereby causing the CP muscle to contract and dilate. This dilation advantageously allows first segment 38 of deployment device 14 to enter the CP muscle region. Continued insertion of the probe, and thus device 14 into the canal, e.g. the esophagus, causes lobe 44 to contract and interact with the CP muscle; through appropriate dimensioning of lobe 44, such interaction causes the CP muscle to relax and constrict. This constriction together with further insertion of the probe tends to cause the CP muscle to constrict further and substantially surround joining section 40 about region 61. Further insertion of probe 10 thus tends to be inhibited, in large part due to the appropriate dimensioning of lobe 46 and of segment 40. With further movement inhibited, said pairs of delivery and sensing electrodes are suitably deployed into the esophagus. Lobes 44 and 46 thus prevent deployment device 14 from migrating up or down the esophagus once probe 10 is in place thereby allowing substantially stable bioimpedance measurements.

More particularly, and in accordance with a particularly preferred aspect of this embodiment of the present invention, lobes 44 and 46 and segments 38, 40 and 42 are suitably configured to encourage this stabilization and securing of device 14 into the CP muscle region. In general, segment 38 and lobe 44 are suitably dimensioned to occasion first contraction (ie. dilation) of the CP muscle, and thereafter as lobe 44 passes into the CP muscle region, relaxation (i.e. contraction) of the CP muscle. Segment 40 and lobe 46, on the other hand, are, in general, preferably dimensioned to prevent further insertion of probe 10 and more preferably once such insertion is halted, to stabilize and prevent further natural movement of device 14 as may be occasioned by, for example, peristaltic movements within the CP muscle region. The result is the stabilization of device 14 to allow positioning of the prominent-arena electrodes within an optimal region of the esophagus.

The various radii that define the various surfaces, particularly surfaces 52, 56, 60, 61 and 62, are also suitably selected to aid in and enhance such operation. Preferably, radius $R_1$ is selected to encourage dilation of the muscle, and thus preferably is in the range of about 2.0 to about 3.0 cm, optimally about 2.54 cm. Similarly, radius $R_2$ preferably is in the range of about 2.0 to about 3.0 cm, optimally about 2.54 cm.

Preferably, radius $R_3$ is selected to encourage contraction of the muscle, and thus preferably is in the range of about 0.04 to about 1.4 cm, and more preferably in the range of about 0.85 to about 1.1 cm, and optimally about 0.953 cm. Preferably, radii $R_4$, $R_5$ and $R_6$ are selected to prevent further movement, either by insertion of probe 10 or by natural peristaltic movements of the muscle, of device 14 once suitably positioned. Accordingly, preferably radius $R_4$ is suitably in the range of about 0.75 to about 1.5 cm, and more preferably in the range of about 0.9 to about 1.1 cm, and optimally about 1.01 cm. Preferably, radius $R_5$ is suitably in the range of about 0.25 to about 0.75 cm, more preferably in the range of about 0.4 to about 0.6 cm, and optimally about 0.477 cm. Finally, radius $R_6$ is generally in the range of about 0.4 to about 1.2 cm, and more preferably in the range of about 0.7 to about 0.9 cm, and optimally about 0.8 cm.

The other dimensions and configurations of the various surfaces of device 14 also are preferably optimized to aid in utilization of probe 10 including device 14. Thus, in accordance with a preferred aspect of this embodiment of the present invention, deployment device 14 preferably evidences a length in the range of about 2 to about 10 cm, more preferably in the range of about 5 to about 8 cm, and optimally about 6.99 cm. First segment 38 preferably evidences a length from leading edge 50 to the crest of lobe 44 which is in the range of about 1 to about 4 cm, more preferably in the range of about 2 to about 3 cm, and optimally about 2.54 cm. Similarly, third segment 42 preferably evidences a length from trailing edge 54 to the crest of lobe 46 which is generally in the range of about 1 to about 4 cm, and more preferably in the range of about 2 to about 3 cm, and optimally about 2.29 cm. Segment 40 preferably evidences a length from the crest of lobe 44 to the crest of lobe 46 which is generally in the range of about 0.25 to about 0.75 cm and more preferably in the range of about 0.35 to about 0.53 cm, and optimally about 0.445 cm.

In accordance with a preferred aspect of this embodiment of the present invention, lobes 44 and 46 are also suitably configured to enhance use. Accordingly, the lobes 44 and 46 preferably evidence (at their respective crests) a diameter in the range of about 0.5 to about 2.5 cm, more preferably in the range of about 1.2 to about 2 cm and optimally about 1.6 cm. It should be understood that, lobes 44 and 46 may have different diameters. For example, in accordance with a further aspect of the present invention, it may be beneficial for lobe 46 to evidence a diameter greater than the diameter of lobe 44.

To aid with insertion, leading edge 50 preferable evidences a diameter which is advantageously smaller than the diameter of lobes 44 and 46. In accordance with a in preferred aspect of this embodiment, leading edge 50 evidences a diameter which is in the range of about 0.2 to about 1.5 cm, more preferably in the range of about 0.8 to about 1 cm, and optimally about 0.89 cm. In addition, preferably the outermost portion of leading edge 48 is rounded so that it can pass through the esophageal canal with relative ease. While not necessarily important for effective use of device 14, preferably, trailing edge 54 is similarly dimensioned, and thus preferably is also rounded at its outermost portion and evidences a diameter on the order of about 0.2 to about 1.5 cm, optimally about 0.89 cm.

While the preferred dimensions and configuration of device 14 have now been described, it should be appreciated that device 14 suitably may evidence a wide variety of different configurations, providing such configurations also enable proper placement and securing of probe 10 in a suitable region of the anatomical canal in which probe 10 is inserted. For example, in accordance with one alternate aspect of the invention, segment 42 may be omitted. Further alterations and modifications of the dimensions and configurations of the various segments and regions of device 14 may also be made, as will be appreciated or as may be hereafter devised by those skilled in the art in light of this disclosure.

With continued reference to FIGS. 4A and 4B, in accordance with a preferred aspect of this embodiment of the present invention, device 14 preferably evidences an axial lumen 65. Preferably, lumen 65 is substantially cylindrical and extends from leading edge 50 to trailing edge 54. Preferably, lumen 65 evidences a generally uniform diameter on the order of about 0.5 to about 0.75 cm, and optimally about 0.635 cm. Preferably, device 14 is mounted to chassis 12 such that chassis 12 extends through lumen 65. Alternatively, however, particularly in cases where probe 10 is configured to operate without an acoustic device, lumen 65 may be suitably eliminated and chassis 12 merely attached to device 14, such as, for example, in proximity to trailing edge 54.

With reference again to FIG. 1, in accordance with a preferred aspect of this embodiment of the present invention, device 14 is suitably employed in connection with probe 10 such that effective and reliable bioimpedence measurements are obtained when probe 10 is inserted into the esophagus; that is, insertion of probe 10 into the patient results in effective placement of electrode assembly 16 proximate the esophagus.

Preferably, to correctly position deployment device 14 at the CP muscle region, the center of segment 40 of device 14 is suitably positioned at a distance from proximal end 15 in the range of about 15 to about 35 cm, preferably about 25 to about 30 cm, and most preferably about 26 to about 28 cm. Acoustic diaphragm 24 is suitably located at distal end 13 of probe 10, and may as previously noted, suitably enclose temperature measuring device 36 without eliminating the effectiveness of thermistor 36.

It should be noted that the lengths disclosed herein are exemplary measurements suitable for use of a probe in accordance with the present invention configured for insertion into a human esophagus, and that the invention is not limited to these dimensions. The anatomical structure of other animals or other anatomical canals may cause the dimensions to vary accordingly.

To aid in proper insertion of probe 10, chassis 12 may include indicia useful for visually determining when probe 10 has been fully and properly inserted into an anatomical canal. Thus, in accordance with a further aspect of the present invention, probe 10 comprises a depth marker 29 which can serve as an indicator as to when probe 10 is inserted a proper distance. Depth marker 29 suitably may be placed on chassis 12 such that when it is at the mouth area, deployment device 14 is near the CP muscle region, and acoustic diaphragm 24 and temperature measuring device 36 are in their appropriate locations. Depth marker 29 may comprise indicia, such as markings, surface impressions, etc., formed on chassis 12. Preferably, depth marker 29 is positioned on chassis 12 a predetermined distance from proximal end 15 in the range of about 7 to about 20 cm, preferably about 10 to about 17 cm, and most preferably about 12 to about 14 cm.

In accordance with an alternative embodiment of the present, acoustic adapter 28 may be replaced with a handle to aid in insertion of probe 10 into an anatomical canal, or a handle (not shown) may be used in addition to adapter 28. Such a handle, in either case, suitably is attached to proximal end 15 of probe 10.

Having now described the various aspects of probe 10, a preferred manner of inserting probe 10 into a patient will now be described with reference to FIG. 5. In accordance with a preferred embodiment of the present invention, a person (e.g. doctor, technician, etc.) will insert probe 10 through the mouth and into an esophageal cavity 90 of a patient causing leading edge 13, temperature measuring device 36 and acoustic diaphragm 24, etc. to pass down esophagus 90 to and through the CP muscle region 92. As probe 10 is further inserted, deployment device 14 is directed toward CP muscle 92. Because deployment device 14 is larger than chassis 12, leading edge 50 of deployment device 14 will generally stretch the membrane that precedes (i.e. is above) muscle 92, thereby causing activation of the neurons in the muscle and thus relaxation (ie. dilation) of muscle 92. Continued insertion of probe 10 results in lobe 44 being passed through muscle 92, which in turn tends to cause muscle 92 to contract and generally surround segment 40 of device 14. While insertion of probe 10 may halt at that point, preferably probe 10 is further inserted such that lobe 46 is also passed through muscle 92. In accordance with this aspect of the present invention, to thus set deployment device 14 of probe 10 in place, the direction of probe 10 is thereafter reversed such that lobe 46 backs up through CP muscle 92. Such movement tends to cause CP muscle 92 to relax and constrict upon segment 40. This constriction of muscle 92 tends to "lock" device 14 in place thus tending to deploy said delivery and sensing electrodes in an ideal location. In addition, due to the orientation of the elements of probe 10, once device 14 is suitably positioned, acoustic diaphragm 24 and thermistor 36 will also be suitably positioned further within esophagus 90. This approximate positioning may be evident by alignment of a depth marker 29 within the mouth of the patient.

It will be understood that the foregoing description is of preferred exemplary embodiments of the invention, and that the invention is not limited to the specific forms shown. Various modifications may be made in the design and arrangement of the elements set forth herein without departing from the scope of the invention as expressed in the appended claims.

We claim:

1. An esophageal probe useful for invasively monitoring cardiac functions in the esophagus of a patient, the probe comprising:
    a chassis having a proximal end and a distal end;
    a deployment device configured with said chassis, wherein said deployment device is configured to reside in the crico-pharyngeal muscle region of the esophagus to stabilize the probe in the esophagus; and
    an electrode assembly comprising a plurality of electrodes, all of said plurality of electrodes being located outside of said deployment device and being positioned between said deployment device and said distal end of said chassis to maintain contact with the esophagus.

2. A probe in accordance with claim 1, wherein said electrodes comprise at least one pair of electrodes for delivery of alternating current and at least one pair of electrodes for sensing voltage abstract associated with an impedance related to a patients thorax.

3. A probe in accordance with claim 1, wherein each electrode comprises:
    a conductive band having an outside surface and being configured for attaching to said chassis; and
    a contact surface located on said outside surface of the conductive band, said contact surface configured to interface with the esophagus.

4. A probe in accordance with claim 1, wherein said probe further comprises an acoustic diaphragm connected to said chassis for monitoring sounds within the esophagus.

5. A probe in accordance with claim 1, wherein said probe further comprises a temperature measuring device connected to said chassis for measuring temperature within the esophagus.

6. An esophageal probe for invasively monitoring cardiac functions in the esophagus of a patient, the probe comprising:
    a chassis having a proximal end and a distal end;
    a deployment device configured with said chassis to limit movement of the probe within the esophagus, said deployment device having a circumferentially symmetrical hour-glass configuration; and an electrode assembly comprising a plurality of electrodes located between said deployment device and said distal end of said chassis, said plurality of electrodes configured to maintain contact with the esophagus.

7. A probe in accordance with claim 6, wherein said electrodes comprise at least one pair of electrodes for delivery of a first signal and at least one pair of electrodes for sensing a second signal associated with an impedance related to the patient.

8. A probe in accordance with claim 6, wherein each electrode comprises a protruding contact located on an outside surface of said each electrode.

9. A probe in accordance with claim 6, wherein said electrode assembly further comprises an electrical plug assembly and a cable, said cable extending from said proximal end of said chassis and being connected to said electrical plug assembly.

10. A probe in accordance with claim 6, wherein said probe further comprises an acoustic diaphragm connected to said chassis for monitoring sounds within the esophagus.

11. A probe in accordance with claim 6, wherein said probe further comprises a temperature measuring device connected to said chassis for measuring temperature within the esophagus.

12. An esophageal probe for invasively monitoring cardiac functions in the esophagus of a patient, the probe comprising:

a chassis having a proximal end and a distal end;

a deployment device configured with said chassis to stabilize the probe within the esophagus, said deployment device having a circumferentially symmetrical hour-glass configuration; and at least one electrode located between said deployment device and said distal end of said chassis, said at least one electrode being configured to maintain contact with the esophagus.

13. A probe in accordance with claim 12, wherein said deployment device comprises:

a first lobe having a crest and a substantially smooth outer surface;

a first segment having a leading edge and a generally sloped outer surface terminating at said crest of said first lobe; and a second segment having a trailing edge and a generally sloped outer surface terminating at the crest of said first lobe.

14. A probe in accordance with claim 12, wherein said at least one electrode comprises a protruding contact located on an outside surface of said at least one electrode.

15. A probe in accordance with claim 12, wherein said probe further comprises an electrical plug assembly and a cable, said cable extending from said proximal end of said chassis and being connected to said electrical plug assembly.

16. A probe in accordance with claim 12, wherein said probe further comprises an acoustic diaphragm connected to said chassis for monitoring sounds within the esophagus.

17. A probe in accordance with claim 12, wherein said probe further comprises a temperature measuring device connected to said chassis for measuring temperature within the esophagus.

* * * * *